United States Patent
Hillman et al.

(10) Patent No.: US 11,737,457 B2
(45) Date of Patent: *Aug. 29, 2023

(54) ANTIMICROBIAL AND FOAMABLE ALCOHOLIC COMPOSITIONS

(71) Applicant: GOJO Industries, Inc., Akron, OH (US)

(72) Inventors: Evan D. Hillman, North Canton, OH (US); Daniel J. Lacks, Shaker Heights, OH (US); Mitchell J. Cohen, Salisburg, NC (US)

(73) Assignee: GOJO Industries, Inc., Akron, OH (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/864,315

(22) Filed: May 1, 2020

(65) Prior Publication Data

US 2020/0253198 A1 Aug. 13, 2020

Related U.S. Application Data

(63) Continuation of application No. 16/177,489, filed on Nov. 1, 2018, now Pat. No. 10,674,722, which is a continuation of application No. 14/380,183, filed as application No. PCT/US2013/027314 on Feb. 22, 2013, now abandoned.

(60) Provisional application No. 61/644,595, filed on May 9, 2012, provisional application No. 61/621,763, filed on Apr. 9, 2012, provisional application No. 61/602,834, filed on Feb. 24, 2012.

(51) Int. Cl.
| | | |
|---|---|---|
| *A01N 25/30* | (2006.01) | |
| *A01N 31/02* | (2006.01) | |
| *A01N 25/16* | (2006.01) | |
| *C07F 7/08* | (2006.01) | |

(52) U.S. Cl.
CPC ............. *A01N 25/30* (2013.01); *A01N 25/16* (2013.01); *A01N 31/02* (2013.01); *C07F 7/0829* (2013.01)

(58) Field of Classification Search
CPC ........ A01N 25/30; A01N 25/16; A01N 31/02; C07F 7/0829
See application file for complete search history.

(56) References Cited

U.S. PATENT DOCUMENTS

| | | |
|---|---|---|
| 3,069,319 A | 12/1962 | Stearns |
| 3,954,960 A | 5/1976 | Valan |
| 4,933,177 A | 6/1990 | Grollier et al. |
| 4,956,170 A | 9/1990 | Lee |
| 4,961,921 A | 10/1990 | Chuang et al. |
| 5,167,950 A | 12/1992 | Lins |
| 5,266,598 A | 11/1993 | Ninomiya et al. |
| 5,340,570 A | 8/1994 | Wong et al. |
| 5,658,552 A | 8/1997 | Bunning et al. |
| 5,714,135 A | 2/1998 | Lee et al. |
| 5,968,204 A | 10/1999 | Wise |
| 5,985,294 A | 11/1999 | Peffly |
| 6,080,417 A | 6/2000 | Axel et al. |
| 6,096,297 A | 8/2000 | Jones et al. |
| 6,096,349 A | 8/2000 | Petri et al. |
| 6,123,953 A | 9/2000 | Greff |
| 6,582,711 B1 | 6/2003 | Asmus |
| 6,793,914 B2 | 9/2004 | Clarkson et al. |
| 7,199,090 B2 | 4/2007 | Koivisto et al. |
| 7,247,295 B2 | 7/2007 | Schmaus et al. |
| 7,384,646 B2 | 6/2008 | Kobayashi et al. |
| 7,566,460 B2 | 7/2009 | Asmus et al. |
| 7,582,681 B2 | 9/2009 | Schmaus et al. |
| 7,632,871 B2 | 12/2009 | Kobayashi et al. |
| 2001/0018535 A1 | 8/2001 | Klein |
| 2004/0228820 A1 | 11/2004 | Elliott et al. |
| 2005/0222001 A1 | 10/2005 | Baumeister |
| 2005/0222276 A1 | 10/2005 | Schmaus et al. |
| 2005/0228032 A1 | 10/2005 | Merianos et al. |
| 2007/0059331 A1 | 3/2007 | Schmaus et al. |
| 2007/0065385 A1 | 3/2007 | Porter |
| 2007/0082039 A1 | 4/2007 | Jones, Jr. et al. |
| 2007/0184013 A1 | 8/2007 | Snyder et al. |
| 2007/0185216 A1 | 8/2007 | Snyder et al. |
| 2007/0265352 A1 | 11/2007 | Roeding et al. |
| 2009/0004122 A1 | 1/2009 | Modak et al. |
| 2009/0018213 A1 | 1/2009 | Snyder et al. |
| 2009/0082472 A1 | 3/2009 | Peters |
| 2009/0175806 A1 | 7/2009 | Modak et al. |
| 2009/0227675 A1 | 9/2009 | Lindstrom et al. |

(Continued)

FOREIGN PATENT DOCUMENTS

| | | |
|---|---|---|
| EP | 0796610 A1 | 9/1997 |
| EP | 1764135 A1 | 3/2007 |

(Continued)

OTHER PUBLICATIONS

Chatterjee et al., Appl. Environ. Microbio. Apr. 2006; 72(4): 2627-2636.*
Bis-PEG-18 Methyl Ether Dimethyl Silane, CosDNA, URL <http://www.cosdna.com/cht/c6036110710.html>, downloaded on Dec. 19, 2016.
European Search Report for European Application No. EP10165683 dated Sep. 5, 2012; 6 pages.
International Search Report and Written Opinion of the International Searching Authority for technology related International Appl. No. PCT/US2008/081502 dated Dec. 16, 2010; 13 pages.
International Search Report for International Appl. No. PCT/US2010/038453 dated Feb. 23, 2011; 3 pages.

(Continued)

*Primary Examiner* — Alicia L Otton
(74) *Attorney, Agent, or Firm* — Calfee, Halter & Griswold LLP

(57) ABSTRACT

Antimicrobial and foamable alcoholic compositions, where the compositions include at least about 40 wt. % of a $C_{1-4}$ alcohol and one or more silane surfactants selected from (1) zwitterionic silane surfactants, (2) polyalkoxylated silane surfactants that contain at least one silane group and at least one polyalkylene oxide chain.

8 Claims, No Drawings

(56) References Cited

U.S. PATENT DOCUMENTS

| | | |
|---|---|---|
| 2009/0238787 A1 | 9/2009 | Finke et al. |
| 2010/0068161 A1 | 3/2010 | Todary |
| 2010/0317743 A1 | 12/2010 | Macinga et al. |
| 2014/0370182 A1 | 12/2014 | Makiko |

FOREIGN PATENT DOCUMENTS

| | | |
|---|---|---|
| EP | 1769824 A1 | 4/2007 |
| EP | 1967576 A1 | 9/2009 |
| EP | 2210662 A3 | 6/2011 |
| JP | 89971/95 | 4/1995 |
| JP | H8-034712 | 9/1997 |
| JP | 11322591 | 11/1999 |
| JP | 2004352688 A | 12/2004 |
| JP | 2005-526036 A | 9/2005 |
| JP | 2006273719 A | 10/2006 |
| JP | 2007145750 A | 6/2007 |
| JP | 2007176940 | 7/2007 |
| JP | 2007-532542 A | 11/2007 |
| JP | 2008546692 | 12/2008 |
| KR | 1020080108972 A | 12/2008 |
| WO | 9939687 A1 | 8/1999 |
| WO | 9956715 A1 | 11/1999 |
| WO | 03003998 A1 | 1/2003 |
| WO | 2005030917 A1 | 4/2005 |
| WO | 20051022276 A1 | 11/2005 |
| WO | 2006033970 A2 | 3/2006 |
| WO | 2006138111 A1 | 12/2006 |
| WO | 2007063065 A1 | 6/2007 |
| WO | 2008067028 A2 | 6/2008 |
| WO | 2008076839 A3 | 6/2008 |
| WO | 2008132621 A1 | 11/2008 |
| WO | 2008135085 A1 | 11/2008 |
| WO | 2010091327 A2 | 8/2010 |
| WO | 2010147868 A2 | 12/2010 |
| WO | 2011084661 A3 | 7/2011 |
| WO | 2017069157 A1 | 4/2017 |

OTHER PUBLICATIONS

International Preliminary Reporton Patentability for International Appl. No. PCT/US2010/038453 dated Dec. 16, 2011; 8 pages.
International Search Report and Written Opinion dated Jun. 26, 2014 for PCT/US2012/027314.
Silwax(R) WS, URL, https://www.siltech.com/wp-content/uploades/2017/10/TP2920.pdf.

\* cited by examiner

ANTIMICROBIAL AND FOAMABLE ALCOHOLIC COMPOSITIONS

CROSS-REFERENCE TO RELATED APPLICATIONS

This application is a continuation of U.S. patent application Ser. No. 16/177,489, filed on Nov. 1, 2018, which is a continuation of U.S. patent application Ser. No. 14/380,183, filed on Aug. 21, 2014, which is a national stage entry of International Patent Application Pub. No. PCT/US2013/027314, filed on Feb. 22, 2013, which claims the benefit of U.S. Provisional Patent Application Ser. No. 61/644,595, filed May 9, 2012; U.S. Provisional Patent Application Ser. No. 61/621,763, filed Apr. 9, 2012; and U.S. Provisional Patent Application Ser. No. 61/602,834, filed Feb. 24, 2012, the entire disclosures of which are incorporated herein by reference.

TECHNICAL FIELD

This invention relates to antimicrobial and foamable alcoholic compositions, and more particularly, to alcoholic compositions that include one or more silane surfactants.

BACKGROUND OF THE INVENTION

Foam cleaning products are popular, in part because they are easier to spread on surfaces. Consumers seem to prefer the luxury of foamed soap products. Less foam is needed to produce the same cleaning power as liquids or gels. Properly formulated foam products do not produce the drip and splash that is experienced with traditional gelled or liquid products. This prevents damage to the floors and walls of facilities where the product dispensers are used. Manufacturing of foam products may be easier than gelled products, which often incorporate powdered thickeners that are difficult to handle.

Alcoholic products are popular as sanitizers for the skin. Aesthetics are important, and the user will be more likely to use a product that is not sticky or slimy, and is not harsh on the skin. Several references describe the use of various foaming surfactants for non-aerosol alcoholic foam compositions. However, there is a need for new foaming surfactants that are able to form efficacious, stable, and aesthetically pleasing foamable antimicrobial alcoholic compositions.

SUMMARY OF THE INVENTION

One or more embodiments of this invention provide a foamable composition comprising at least about 40 wt. % of a $C_{1-4}$ alcohol or a mixture of two or more $C_{1-9}$ alcohols, based upon the total weight of the alcoholic composition; and one or more silane surfactants.

One or more embodiments of this invention further provide an antimicrobial composition comprising at least about 50 wt. % of a $C_{1-4}$ alcohol, based upon the total weight of the alcoholic composition; and from about 0.001 to about 10 wt. % of one or more silane surfactants.

DETAILED DESCRIPTION OF ILLUSTRATIVE EMBODIMENTS

In one or more embodiments, alcoholic compositions in accordance with this invention include at least one lower alcohol. In one embodiment, the lower alcohol contains 1 to 4 carbon atoms. Typically, these alcohols have antimicrobial properties. Examples of lower alcohols include, but are not limited to, methanol, ethanol, propanol, isopropanol, butanol, isobutanol, tertiary butanol, and mixtures thereof. In one embodiment, the alcohol comprises ethanol.

The alcoholic composition may include a mixture of $C_{1-9}$ alcohols. In one or more embodiments, the alcoholic composition includes a mixture of one or more $C_{1-4}$ alcohols and one or more $C_{5-9}$ alcohols. The mixture may include primary, secondary, or tertiary alcohols.

Generally, the alcoholic composition comprises an amount of alcohol of at least about 40 weight percent (wt. %), based upon the total weight of the alcoholic composition. In one or more embodiments, the alcoholic composition comprises at least about 45 wt. % alcohol, in other embodiments, at least about 50 wt. % alcohol, in other embodiments, at least about 60 wt. % alcohol, in other embodiments, at least about 62 wt. % alcohol, in other embodiments, at least about 65 wt. % alcohol, in other embodiments, at least about 68 wt. % alcohol, based upon the total weight of alcoholic composition. More or less alcohol may be required in certain instances, depending particularly on other ingredients and/or the amounts thereof employed in the composition. In one or more embodiments, the alcoholic composition comprises from about 40 wt. % to about 98 wt. % alcohol, in other embodiments, the alcoholic composition comprises from about 45 wt. % to about 95 wt. % of alcohol, in yet other embodiments, the alcoholic composition comprises from about 50 wt. % to about 90 wt. % of alcohol, and in still other embodiments, the alcoholic composition comprises from about 55 wt. % to about 80 wt. % of alcohol, based upon the total weight of the alcoholic composition.

The alcoholic compositions of the present invention include one or more silane surfactants. In one or more embodiments, the silane surfactants may contribute foaming properties to the alcoholic composition.

In one or more embodiments, the silane surfactant may be characterized as a zwitterionic silane surfactant. In one or more embodiments, the zwitterionic surfactant includes an ionic portion and a non-polar silane portion. In one or more embodiments, the zwitterionic surfactant may be represented by the formula

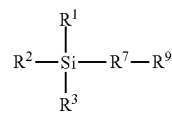

where wherein $R^1$, $R^2$, and $R^3$ are each independently a branched or linear $C_2$ to $C_{20}$ hydrocarbon group, $R^7$ is a divalent hydrocarbon group with about 4 to about 20 carbon atoms and optionally includes one or both of a lateral hydroxyl group and an ether oxygen, and $R^9$ is selected from the group consisting of

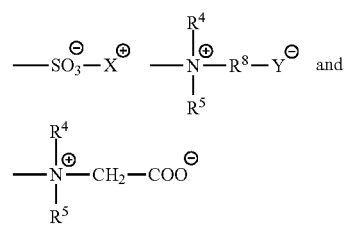

where $R^4$, $R^5$ and $R^8$ are each independently alkyl groups with from 1 to about 6 carbon atoms.

In one or more embodiments, the zwitterionic surfactant includes a polar dimethylglycine portion and a non-polar silane portion. In one or more embodiments, the zwitterionic surfactant includes a betaine moiety and an alkyl silane portion.

In one or more embodiments, the zwitterionic surfactant may be represented by the formula

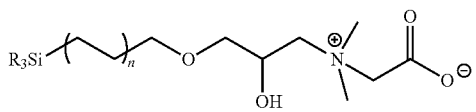

where each R is independently a branched or linear $C_2$ to $C_{20}$ hydrocarbon group. Examples of $C_2$ to $C_{20}$ hydrocarbon groups include alkyl and alkene groups. In one or more embodiments, each R is independently an alkyl group with from 1 to 6 carbon atoms. In one or more embodiments, at least one R is n-butyl, and in other embodiments, at least two R groups are n-butyl.

In one or more embodiments, the zwitterionic silane surfactant is a n-butyl silane surfactant. In one or more embodiments, the n-butyl silane surfactant may be represented by the formula

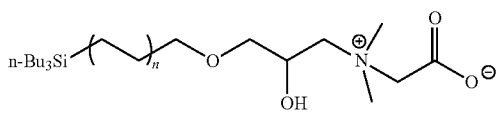

where n is an integer from about 1 to about 20.

In one embodiment, the zwitterionic silane is present in an amount of from about 0.001 to about 10 weight percent, and in another embodiment, from about 0.002 to about 5 weight percent, based upon the total weight of the alcoholic composition. In another embodiment, the zwitterionic silane is present in an amount of from about 0.01 to about 4 weight percent, based upon the total weight of the alcoholic composition. It is envisioned that higher amounts may also be effective to produce foam. All such weights as they pertain to zwitterionic silanes and other ingredients throughout this specification are based on the active level and, therefore do not include carriers or by-products that may be included in commercially available materials, unless otherwise specified.

In other embodiments, it may be desirable to use higher amounts of zwitterionic silane. For example, in certain embodiments where the foaming alcoholic composition of the present invention includes a cleansing or sanitizing product that is applied to a surface and then rinsed off, higher amounts of zwitterionic silane may be employed. In these embodiments, the amount of zwitterionic silane is present in amounts up to about 35 weight percent, based upon the total weight of the composition.

In one or more embodiments, the zwitterionic silane is added directly to the alcoholic composition. In one embodiment, the zwitterionic silane is added to the alcohol, and the mixture is heated, with stirring, until a homogeneous mixture is obtained.

In other embodiments, the zwitterionic silane is added to the alcoholic composition as a solution or emulsion. In other words, the zwitterionic silane may be premixed with a carrier to form a zwitterionic silane solution or emulsion, with the proviso that the carrier does not deleteriously affect the foaming properties of the alcoholic composition. Examples of carriers include water, alcohol, glycols such as propylene glycol, ethylene glycol, and butylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the zwitterionic silane is premixed to form a zwitterionic silane solution or emulsion, the amount of solution or emulsion that is added to the alcoholic composition may be selected so that the amount of zwitterionic silane falls within the ranges set forth hereinabove.

In one or more embodiments, the n-butyl silane surfactant may be prepared by a two-step reaction process shown in Scheme 1 below.

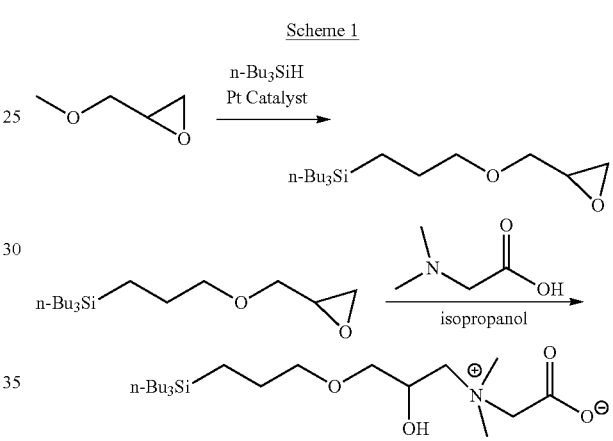

The reaction shown in Scheme 1 utilizes a platinum catalyst. More generally, the synthesis includes the following reaction scheme: a) epoxides, which have a olefinic double bond, are reacted by means of an addition reaction in the presence of a hydrosilylation catalyst with a silanes and b) the epoxide ring of the silane-modified epoxides is opened by a known reaction and the product obtained is b1) sulfonated, or b2) quaternized by reaction with a tertiary amine in the presence of an acid YH, or b3) converted into a betaine by a reaction with a compound of the formula

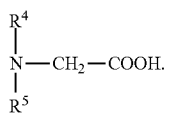

Preferably, the hydrosilylation is carried out at an elevated temperature and/or in the presence of a solvent, a platinum catalyst being used as catalyst.

Step b1) of the method is carried out in a known manner by reacting the silane-modified epoxides with alkali sulfite/alkali hydrogen sulfate or by reacting the sulfite/hydrogen sulfate of the desired cation in the presence of a polar solvent. As solvent, an isopropanol/water mixture is preferably used. The reaction preferably is carried out at an elevated temperature, for example, at the boiling point of the isopropanol/water mixture.

Step b2) of the method, namely the reaction of silane-modified epoxides with different tertiary amines also is preferably carried out in the presence of a polar solvent, particularly a short-chain, low-boiling, aliphatic alcohol, such as isopropanol. The reaction proceeds in the presence of a protonic acid, acetic acid being preferred.

Step b3) of the method comprises the reaction of the silane-modified epoxides with dialkylaminoacetic acid in the presence of a polar solvent, particularly, a lower molecular weight aliphatic alcohol, such as isopropanol.

It is also possible to react the silane-modified epoxide initially with a dialkylamine, such as dimethylamine in an equivalent manner and then to convert the product obtained by reaction with sodium chloroacetate in the presence of a polar solvent, such as isopropanol, into the betaine.

A similar synthesis procedure is described in U.S. Pat. No. 6,489,498, which is incorporated herein by reference.

In one or more embodiments, the zwitterionic surfactant may be prepared by a process comprising the steps of (a) reacting an epoxide by means of an addition reaction in the presence of a hydrosilylation catalyst with a silane of the general formula

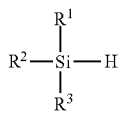

to form a silane-modified epoxide having an epoxide ring; and (b) reacting the silane-modified epoxide with a compound of the general formula

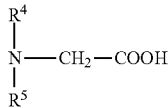

to form a betaine of the general formula

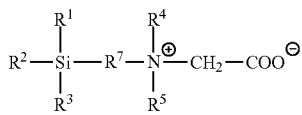

wherein $R^1$, $R^2$, and $R^3$ are each independently a branched or linear $C_2$ to $C_{20}$ hydrocarbon group, $R^7$ derives from the epoxide, and is a divalent hydrocarbon group with about 4 to about 20 carbon atoms and optionally includes a lateral hydroxyl group, and optionally includes an ether oxygen, and $R^4$ and $R^5$ are each independently selected from alkyl groups with 1 to about 6 carbon atoms.

The silane surfactant may be a liquid or a solid at standard conditions of temperature and pressure. In one or more embodiments, the silane surfacant is a waxy solid at standard conditions of temperature and pressure.

In one or more embodiments, the silane surfactant is a polyalkoxy silane surfactants, and may be described as a molecule that contains at least one silane group and at least one polyalkylene oxide chain. The at least one silane group may be described as a moiety that includes a silicon atom bonded directly to a hydrogen atom or a carbon atom. The polyalkylene oxide chain may include ethylene oxide units, propylene oxide units, or a mixture thereof. In one or more embodiments, the silane surfactant may thus be referred to as a polyethoxylated (PEG) and/or polypropoxylated (PPG) silane surfactant, i.e. a polyalkoxy silane surfactant.

In one or more embodiments, the polyalkoxy silane surfactant may include from 1 to about 100 units of polyalkylene oxide per molecule of surfactant, in other embodiments, from about 5 to about 90 units of polyalkylene oxide per molecule of surfactant, in other embodiments, from about 10 to about 80 units of polyalkylene oxide per molecule of surfactant, and in other embodiments, from about 20 to about 60 units of polyalkylene oxide per molecule of surfactant, and in other embodiments.

Examples of alkoxylated silane surfactants include those designated according to the International Nomenclature of Cosmetic Ingredients (INCI) as bis-peg-18 methyl ether dimethyl silane.

In one or more embodiments, the molecular weight distribution (Mw/Mn) of the silane surfactant is less than about 2.4, in other embodiments less than about 2.2, in yet other embodiments less than about 2.0, in other embodiments, less than about 1.8. Molecular weight and molecular weight distribution may be measured by conventional techniques, including gel permeation chromatography (GPC).

In one or more embodiments, the melting point of the silane surfactant is from about 29 to about 35° C.

As is known in the art, surface energy values for solid materials may be calculated based upon contact angles between the solid and a liquid, or set of liquids. The surface energy is often described as comprised of two components—a dispersive component and a polar component, where the dispersive component theoretically accounts for van der Waals and other non-site specific interactions that a surface is capable of having with applied liquids, and the polar component theoretically accounts for dipole-dipole, dipole-induces dipole, hydrogen bonding, and other site-specific interactions which a surface is capable of having with applied liquids.

The Fowkes method for measuring surface energy is further described in Fowkes, F. M., "Industrial and Engineering Chemistry," 56, 12, 40 (1964). Generally, the samples to be measured are melted, and poured out onto a flat substrate and re-solidified to create a flat surface. Drops of water and diiodomethane are placed on the flat surface and measured for contact angle within a short amount of time, such that the drops have spread to characteristic contact angles but not yet soaked into the sample significantly. The angles may be measured with, for example, a Kruss Drop Shape Analysis system DSA 100. From the water and diiodomethane contact angle measurements, and using Fowkes theory, surface energies may be calculated, including overall surface area, a polar component, and a dispersive component. The percentage of the overall surface energy that is due to surface polarity may be calculated based upon these numbers.

In one or more embodiments, the surface energy of the silane surfactant, when measured according to the Fowkes method at 22° C., and using water and diiodomethane, is less than about 23 dynes/cm, in other embodiments, less than about 22.5 dynes/cm. In one or more embodiments, the surface energy of the silane surfactant, when measured according to the Fowkes method at 22° C., is from about 21 to about 23 dynes/cm.

In one or more embodiments, the polar component of the surface energy at about 22° C. is less than about 2.5 dynes/cm, in other embodiments, less than about 2.2 dynes/ cm. In one or more embodiments, the polar component is from about 1.7 to about 2.2 dynes/cm.

In one or more embodiments, the percentage of the surface energy that is due to surface polarity at about 22° C. is less than about 10%, in other embodiments, less than about 9.5%, in other embodiments, less than about 9%.

In one or more embodiments, the surface energy of the silane surfactant, when measured according to the Fowkes method at about 40° C., is less than about 21 dynes/cm, in other embodiments, less than about 20.8 dynes/cm. In one or more embodiments, the surface energy of the silane surfactant, when measured according to the Fowkes method at 40° C., is from about 20 to about 21 dynes/cm.

In one or more embodiments, the polar component of the surface energy at about 40° C. is less than about 1.5 dynes/cm, in other embodiments, less than about 1.4 dynes/cm. In one or more embodiments, the polar component is from about 1.0 to about 1.5 dynes/cm.

In one or more embodiments, the percentage of the surface energy that is due to surface polarity at about 40° C. is less than about 7%, in other embodiments, less than about 6.5%.

In one or more embodiments, the silane is present in an amount of from about 0.001 to about 20 wt. %, in other embodiments, from about 0.005 to about 15 wt. %, in other embodiments, from about 0.01 to about 10 wt. %, based upon the total weight of the alcoholic composition. In other embodiments, the silane is present in an amount of from about 0.05 to about 4 wt. %, based upon the total weight of the alcoholic composition. It is envisioned that higher amounts may also be effective to produce foam. All such weights as they pertain to silanes and other ingredients throughout this specification are based on the active level and, therefore do not include carriers or by-products that may be included in commercially available materials, unless otherwise specified.

In one or more embodiments, the silane is added directly to the alcoholic composition. In one embodiment, the silane is added to the alcohol, or to an alcohol/water mixture, with stirring, until a homogeneous mixture is obtained. In one embodiment, the silane is added to the alcohol, or to an alcohol/water mixture, and the mixture is heated, with stirring, until a homogeneous mixture is obtained. In other embodiments, where the silane is a solid at standard conditions of temperature and pressure, the silane may be heated to a temperature above the melting point prior to mixing.

In other embodiments, the silane is added to the alcoholic composition as a solution or emulsion. In other words, the silane may be premixed with a carrier to form a silane solution or emulsion, with the proviso that the carrier does not deleteriously affect the antimicrobial or foaming properties of the alcoholic composition. Examples of carriers include water, alcohol, glycols such as propylene glycol, ethylene glycol, and butylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the silane is premixed to form a silane solution or emulsion, the amount of solution or emulsion that is added to the alcoholic composition may be selected so that the amount of silane falls within the ranges set forth hereinabove.

In one or more embodiments, the alcoholic compositions may further include one or more additional foaming surfactants, such as those described in U.S. Patent Application Publication Nos. 2007/0148101 A1 and 2008/0207767, both of which are hereby incorporated by reference.

In one or more embodiments, the alcoholic compositions further include a siloxane polymer surfactant. Siloxane polymer surfactants include organopolysiloxane dimethicone polyols, silicone carbinol fluids, silicone polyethers, alkylmethyl siloxanes, amodimethicones, trisiloxane ethoxylates, dimethiconols, quaternized silicone surfactants, polysilicones, silicone crosspolymers, and silicone waxes.

Examples of siloxane polymer surfactants include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG 23/PPG 6 dimethicone, PEG 20/PPG 23 dimethicone, PEG 17 dimethicone, PEGS/PPG3 methicone, bis PEG20 dimethicone, PEG/PPG20/15 dimethicone copolyol and sulfosuccinate blends, PEG-8 dimethicone\dimmer acid blends, PEG-8 dimethicone\fatty acid blends, PEG-8 dimethicone \cold pressed vegetable oil\polyquaternium blends, random block polymers and mixtures thereof.

In one embodiment, the siloxane polymer surfactant includes a compound that may be represented by the formula

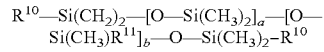

where $R^{10}$ and $R^{11}$ independently include a methyl group or a moiety that may be represented by the formula

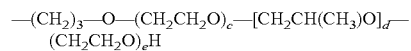

with the proviso that both $R^{10}$ and $R^{11}$ are not $CH_3$, where a is an integer from about 3 to about 21, b is an integer from about 1 to about 7, c is an integer from about 0 to about 40, d is an integer from about 0 to about 40, and e is an integer from about 0 to about 40, with the proviso that a ≥3×b and that c+d+e≥5.

In one or more embodiments, the alcoholic composition includes at least about 0.002 wt. % of siloxane polymer surfactant, based upon the total weight of the alcoholic composition. In another embodiment, the alcoholic composition includes at least about 0.01 wt. % of siloxane polymer surfactant, based upon the total weight of the alcoholic composition. In yet another embodiment, the alcoholic composition includes at least about 0.05 wt. % of siloxane polymer surfactant, based upon the total weight of the alcoholic composition.

In one embodiment, the siloxane polymer surfactant is present in an amount of from about 0.002 to about 4 weight percent, based upon the total weight of the alcoholic composition. In another embodiment, the siloxane polymer surfactant is present in an amount of from about 0.01 to about 2 weight percent, based upon the total weight of the alcoholic composition. All such weights as they pertain to listed ingredients are based on the active level and, therefore, do not include carriers or by-products that may be included in commercially available materials, unless otherwise specified.

The presence of siloxane polymer surfactants, or other secondary foaming surfactants is not necessary to the alcoholic compositions of the present invention, and in certain embodiments, the amount of secondary foaming surfactant in the compositions of the present invention is limited. In one or more embodiments, the compositions include less than about 0.5 wt. % of secondary foaming surfactants, in other embodiments, less than about 0.2 wt. % of secondary foaming surfactants, in other embodiments, less than 0.1 wt. % of secondary foaming surfactants, in other embodiments, less than 0.05 wt. % of secondary foaming surfactants, based upon the total weight of the composition. In other embodiments, the compositions are devoid of additional foaming surfactants.

In certain embodiments, the alcoholic composition of the present invention optionally includes at least one foam enhancer, which may be referred to as a primary foam enhancer. In one or more embodiments, the alcoholic composition of these embodiments exhibits improved foam stability when compared to an alcoholic composition without the foam enhancer. By "foam stability" is meant the length of time that it takes for a foam to break down into a liquid.

In these or other embodiments, the alcoholic composition of these embodiments exhibits improved foam quality when compared to an alcoholic composition without the foam enhancer. By "foam quality" is meant the quantity and size of the foam bubbles. Foams with improved foam quality may be characterized by a greater number of smaller bubbles, which contributes to a creamy, dense appearance.

In one or more embodiments, the primary foam enhancer includes a poly(ethylene oxide) polymer, a poloxamer, hydroxyethyl cellulose, hydroxypropyl cellulose, or a combination thereof.

In one or more embodiments, the primary foam enhancer includes a poly(ethylene oxide) polymer having an average molecular weight in the range from about 100,000 to about 10,000,000, in other embodiments from about 200,000 to about 4,000,000. In one or more embodiments, the primary foam enhancer includes a poly(ethylene oxide) polymer selected from PEG-4 to PEG-100. Examples of commercially available poly(ethylene oxide) polymers suitable for use as a foam enhancer include POLYOX™ products, available from Dow Chemical, such as WSR N-80, WSR N12K, WSR N60K, and WSR-301.

In one or more embodiments, the composition includes up to about 10 wt. % of the primary foam enhancer. In one or more embodiments, the composition includes from 0 to about 10 wt. %, in other embodiments, from about 0.001 to about 8 wt. %, in other embodiments, from about 0.01% to about 5%, in other embodiments, from about 0.01% to about 1%.

Secondary foam enhancers that may optionally be included in the compositions of the present invention include hydroxypropyl guar, cetyl hydroxyethylcellulose, ethylhydroxy ethyl cellulose, polyglycerol, polyoxamine, polyacrylamide, polyacrylamidomethylpropane sulfonic acid, polyacrylic acid, polyethylene/isopropyl maleate/malaic acid copolyol, polymethacrylamidopropyltrimonium chloride, polymethacrylamidopropyltrimonium methosulfate, polymethacrylic acid, polyvinyl methyl ether, butylated poly vinyl pyrrolidone, hydroxypropyl methylcellulose; hydroxypropyl cellulose; and n-vinyl lactam polymers and copolymers.

In one or more embodiments, the secondary foam enhancer may be present in an amount of from about 0 to about 8 wt. %, based upon the total weight of the alcoholic composition. In one embodiment, the foam enhancer is present in an amount of from about 0.005 to about 4 wt. %, in another embodiment, the foam enhancer is present in an amount of from about 0.005 to about 1 wt. %, and in yet another embodiment, the foam enhancer is present in an amount of from about 0.01 to about 0.2 wt. %, based upon the total weight of the alcoholic composition.

In one embodiment, the primary and/or secondary foam enhancer is added directly to the alcoholic composition. In one or more other embodiments, the foam enhancer(s) may be added to the alcoholic composition as a solution or emulsion. In other words, the foam enhancer may be premixed with a carrier to form a foam enhancer solution or emulsion, with the proviso that the carrier does not deleteriously affect the foaming properties of the alcoholic composition. Examples of carriers include water, alcohol, glycols such as propylene glycol, ethylene glycol, and butylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the foam enhancer is premixed to form a foam enhancer solution or emulsion, the amount of solution or emulsion that is added to the alcoholic composition is selected so that the amount of foam enhancer falls within the ranges set forth hereinabove.

The alcoholic composition of this invention may further include a wide range of optional ingredients, with the proviso that they do not deleteriously affect the foam forming properties of the alcoholic composition, or the stability of the foam. The CTFA International Cosmetic Ingredient Dictionary and Handbook, Eleventh Edition, 2006, and the 2007 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Non-limiting examples of functional classes of ingredients are described in these references. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, and keratolytics, and the like. In one embodiment, the alcoholic composition further comprises glycerin. In one embodiments, the alcoholic composition further comprises one or more $C_{6-10}$ alkane diol, such as 1,2-octane diol. In one embodiments, the alcoholic composition further comprises glycerin and one or more $C_{6-10}$ alkane diol.

Auxiliary agents may be included in the alcoholic compositions for the purpose of boosting or modifying the foam quality and characteristics, for modifying the feel of the final formulation during rub in and/or dry time, for providing persistence or long-lasting microbial action of the alcohol, for solubilizing other ingredients such as fragrances or sunscreens, and for irritation mitigation. Auxiliary agents include, but are not necessarily limited to, sulfosuccinates, amine oxides, PEG-80 sorbitan laurate, PEG-150 pentaerythrityl tetrastearate, polyglucosides, alcoholamides, sorbitan derivatives, fatty alcohol ethoxylates, quaternary ammonium compounds, amidoamines, sultaines, isothionates, sarcosinates, betaines, polysorbates and fatty alcohol polyethylene glycols.

Examples of polysorbates include polysorbate-20, which may be referred to as polyoxyethylene sorbitan monolaurate; polysorbate-40, which may be referred to as polyoxyethylene sorbitan monopalmitate; polysorbate-60, which may be referred to as polyoxyethylene sorbitan monostearate; and polysorbate-80, which may be referred to as polyoxyethylene sorbitan monooleate. Additional examples of polysorbates includes polysorbate-21, polysorbate-61, polysorbate-65, polysorbate-81, and polysorbate-85.

The amount of auxiliary agent is not particularly limited, so long as it does not deleteriously affect the antimicrobial or foam forming properties of the alcoholic composition, or the stability of the foam. In certain embodiments, one or more auxiliary agents may be present in the foamable alcoholic composition in an amount of from about 0 to about 2 wt. %, based upon the total weight of the alcoholic composition. In other embodiments, one or more auxiliary agents may be present in the foamable alcoholic composition in an amount of from about 0.1 to about 1 wt. %, based upon the total weight of the alcoholic composition.

Although a propellant may be used to produce stable foam, advantageously a propellant is not necessary. In certain embodiments, the amount of propellant is less than about 1000 parts per million by weight, based upon the total weight of the alcoholic composition. In one embodiment, the alcoholic composition is substantially free of propellants, such as hydrocarbon propellants. By substantially free is meant that the amount of propellant in the alcoholic composition is less than about 100 parts per million by weight, based upon the total weight of the alcoholic composition. In one embodiment, the alcoholic composition is devoid of hydrocarbon propellants.

In one embodiment, alcohol is the only active antimicrobial ingredient introduced into the composition, and in this embodiment the amount of auxiliary antimicrobial ingredients is less than about 0.1 wt. %, based upon the total weight of the alcoholic composition. In other embodiments, the composition includes auxiliary antimicrobial agents in addition to alcohol. Examples of auxiliary antimicrobial agents include, but are not limited to, triclosan, also known as 5-chloro-2(2,4-dichlorophenoxy) phenol and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; silver compounds, biguanides such as polyhexamethylene biguanide hydrochloride (PHMB), also known as polyaminopropyl biguanide (PAPB), phenol derivatives, lauric arginate (LAE), povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; $C_{6-10}$ alkane diols, diazolidinyl urea; benzethonium chloride; methylbenzethonium chloride; and mixtures thereof. When used, the auxiliary antimicrobial agents are present in amounts of from about 0.001 to about 4 wt. %, based upon the total weight of the alcoholic composition. In one or more embodiments, the amount of auxiliary antimicrobial agent is from about 0.1 to about 1 wt. %, based upon the total weight of the alcoholic composition.

The alcoholic composition of the present invention may optionally further comprise a wide range of topical drug actives, with the proviso that they do not deleteriously affect the foam forming properties of the alcoholic composition, or the stability of the foam. Examples of topical drug actives include salicylic acid, acetyl salicylic acid, cis-retinoic acid, trans-retinoic acid, N-acetyl-L-cysteine, lipoic acid, azelaic acid, phytic acid, lisophosphotidic acid, tetracycline, ibuprofen, naproxen, acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, benzoyl peroxide, 2,4,4'-trichloro-2-hydroxy diphenyl ether, phenoxyethanol, phenoxypropanol, phenoxyisopropanol, phytic acid, lipoic acid, lisophosphatidic acid, benoxaprofen, flubiprofen, fenoprofen, fenbufen, ketoprofen, indoprofen, priprofen, carprofen, oxaprozin, pranoprofen, miroprofen, tioxaprofen, suprofen, alminoprofen, tiaprofenic acid, fluprofen, bucloxic acid, benzocaine, lidocaine, bupivacaine, chloroprocaine, dibucaine, etidocaine, mepivacaine, tetracaine, dyclonine, hexylcaine, procaine, cocaine, ketamine, pramoxine, phenol, dihydroxyacetone, tyrosine, ethyltryosinate, phospho-DOPA, β-lactim drugs, quinoline drugs, ciprofloxacin, norfloxacin, erythromycin, amikacin, doxycycline, capreomycin, chlorhexidine, chlortetracycline, oxytetracycline, clindamycin, ethambutol, hexamidinee isethionate, metronidazole, pentamidine, gentamicin, kanamycin, lineomycin, methacyclin, methenamine, minocycine, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycicyline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amnanfadine sulfate, octopirox, parachlorometa xylenol, nystatin, tolnaftate, clotrimazole, 2-ethylhexyl p-methoxycinnamate, octyl methoxycinnamate, p-amino benzoate, p-aminobenzoic acid, 2-phenyl benzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, silica, iron oxide, 4-N,N-(2-ethylhexyl)methyl aminobenzoic acid ester of 2,4-dihydroxybenzophenone, 4-N,N-(2-ethylhexyl)methyl aminobenzoic acid ester with 4-hydroxydibenzoylmethane, 4-N,N-(2-ethylhexyl)methyl aminobenzoic acid ester of 2-hydroxy-4-(2-hydroxyethoxy)benzophenone, 4-N,N-(2-ethylhexyl)-methyl aminobenzoic acid ester of 4-(2-hydroxyethoxy)dibenzoylmethane, tetracycline, ibuprofen, naproxen, acetaminophen, alpha-hydroxy acids such as citric acid, lactic acid, and glycolic acid, resorcinol, 3,4,4'- trichlorocarbanilide, octopirox, pharmaceutically-acceptable salts and mixtures of the above. In one embodiment, the alcoholic composition is devoid of drug actives.

In one or more embodiments, the balance of the alcoholic composition includes water or other suitable solvent. In one or more embodiments, the balance of the alcoholic composition comprises a non-aqueous solvent, and the amount of water may be limited. In one embodiment, the amount of water is less than about 20 wt. % of the total weight of the alcoholic composition, in another embodiment, less than about 10 wt. % of the total weight of the alcoholic composition, and in yet another embodiment, less than about 5 wt. % of the total weight of the alcoholic composition.

The alcoholic composition may be prepared by simply mixing the components together. The order of addition is not particularly limited. In one embodiment, the alcoholic composition is prepared by a method comprising dispersing the silane surfactant in the alcohol with slow to moderate agitation, optionally adding water, and then optionally adding other optional ingredients, and mixing until the mixture is homogeneous. In one or more embodiments, the silane surfactant may be heated to liquify the surfactant prior to mixing with the alcohol. In one or more embodiments, the alcohol may be heated to facilitate dissolution of the silane surfactant. In certain embodiments, the mixture may be heated and stirred until a homogeneous solution is obtained. In other embodiments, a homogeneous dispersion or emulsion is obtained.

One or more embodiments of this invention provide a method for forming a non-aerosol alcoholic foam, the method comprising combining a $C_{1-4}$ alcohol or a mixture of two or more $C_{1-9}$ alcohols, one or more silane surfactants, optionally one or more foam enhancers, and optionally other ingredients, to form a foamable alcoholic composition; mixing said alcoholic composition and air or another gas in a mixing chamber to form a mixture; and passing said mixture through a mesh screen, wherein said foamable alcoholic composition comprises at least about 40 percent by weight alcohol, based upon the total weight of the alcoholic composition. Advantageously, one or more embodiments of the present invention form a foam with mixed with air. No propellant or pressurized dispenser system is required.

The foamable compositions of the present invention may be employed in any type of dispenser that can be used for foam products. Advantageously, while the foamable composition can optionally be foamed by aerosolizing the composition, an aerosolized product is not necessary for foaming. Any dispenser that is capable of mixing the foamable alcoholic composition with air or another gas may be used. Other gases that may be used to form the foam include carbon dioxide, nitrogen, argon, xenon, krypton, helium, neon, and radon. In one or more embodiments, the alcoholic composition is used in dispensers that employ foaming pumps, which combine ambient air or another gas and the alcoholic composition under low pressure conditions. In one embodiment, the alcoholic composition may be combined with air or another gas in a mixing chamber, and passed through a mesh screen to form a foam. In this and other embodiments, the viscosity of the composition is less than about 100 mPas, in one embodiment less than about 50 mPas, and in another embodiment less than about 25 mPas, as measured by a Brookfield RV Viscometer using RV and/or LV Spindles at 22° C.+/−3° C.

The alcoholic compositions of the present invention provide disinfecting efficacy, and may be employed on a wide variety of surfaces or substrates, including animate and inanimate surfaces. In one or more embodiments, the present invention provides antimicrobial compositions that may be employed on skin, porous, and non-porous surfaces.

Various modifications and alterations that do not depart from the scope and spirit of this invention will become apparent to those skilled in the art. This invention is not to be duly limited to the illustrative embodiments set forth herein.

We claim:

1. An antimicrobial alcoholic composition comprising:
at least 60 wt. % of an antimicrobial ingredient comprising a $C_{1-4}$ alcohol or a mixture of two or more $C_{1-9}$ alcohols, based upon the total weight of the alcoholic composition; and
a polyalkoxylated silane surfactant consisting of bis-PEG-18 methyl ether dimethyl silane.

2. The alcoholic composition of claim 1, wherein the alcohol comprises methanol, ethanol, propanol, isopropanol, butanol, isobutanol, tertiary butanol, or mixtures thereof.

3. The alcoholic composition of claim 1, wherein the alcoholic composition comprises from 0.01 to 10 wt. % of the polyalkoxylated silane surfactant.

4. The alcoholic composition of claim 3, wherein the alcoholic composition comprises from 0.05 to 4 wt. % of the polyalkoxylated silane surfactant.

5. The alcoholic composition of claim 1, wherein the alcoholic composition comprises at least 65 wt. % of the $C_{1-4}$ alcohol or mixture of two or more $C_{1-9}$ alcohols.

6. The alcoholic composition of claim 1, wherein the alcoholic composition comprises at least 68 wt. % of the $C_{1-4}$ alcohol or mixture of two or more $C_{1-9}$ alcohols.

7. The alcoholic composition of claim 1, wherein the composition further comprises glycerin.

8. The alcoholic composition of claim 1, wherein the composition is a foamable composition.

* * * * *